United States Patent [19]

Hasslinger et al.

[11] 4,088,136
[45] May 9, 1978

[54] SEPARABLE FASTENER FOR CATHETER TUBES AND THE LIKE

[75] Inventors: Russell Hasslinger, Wyckoff; Keldon S. Pickering, Basking Ridge, both of N.J.

[73] Assignee: American Velcro Inc., Manchester, N.H.

[21] Appl. No.: 717,944

[22] Filed: Aug. 26, 1976

[51] Int. Cl.² .......................................... A61M 25/02
[52] U.S. Cl. ...................... 128/349 R; 128/DIG. 26; 24/16 R; 224/5 H
[58] Field of Search ................................ 128/132–134, 128/348–351, DIG. 26, DIG. 15, 165, 171; 224/5 R, 5 H, 26 R; 24/16 R, 73 CC, 73 GS, 81 CC

[56] References Cited

U.S. PATENT DOCUMENTS

| | | | |
|---|---|---|---|
| 2,514,796 | 7/1950 | Rishcoff | 224/5 H |
| 3,297,026 | 1/1967 | Van Pelt | 128/165 X |
| 3,430,300 | 3/1969 | Doan | 128/DIG. 26 |
| 3,677,250 | 7/1972 | Thomas | 128/DIG. 26 |
| 3,726,280 | 4/1973 | Lacount | 128/349 R |
| 3,947,927 | 4/1976 | Rosenthal | 128/DIG. 15 |

*Primary Examiner*—Dalton L. Truluck
*Attorney, Agent, or Firm*—Pennie & Edmonds

[57] ABSTRACT

A separable fastening device is disclosed to support a catheter tube to a limb of a patient. The fastener has a first flexible strap member including a first knitted textile material having upstanding from one surface a plurality of multifilamentary loop-like elements and a polyurethane foam substrate secured to the opposite surface. A second section is formed of a flexible tape member having upstanding from one surface a plurality of hook-like elements which matingly engage with the upstanding filamentary loop-like elements of the first section so as to be attachable thereto at the respective end portions to form a complete flexible strap member. The end portion of the first section is generally tapered at the connection to the second section and defines an opening therethrough spaced sufficiently from the tapered end and dimensioned to receive a free end portion of the second section. The length of the second section and the relative positioning of the opening in the first section are such as to permit the tapered end portion to be looped about the catheter tube while the second tape section extends therethrough so as to be matingly engaged with the loop-like elements of the first section to secure the catheter tube therein and to attach the entire device in position about a limb of a patient. The polyurethane material provides a friction surface which grips the tube in a firm, but gentle manner as well as being capable of gripping the human limb to retain the catheter tube in its precise desired position.

21 Claims, 6 Drawing Figures

SEPARABLE FASTENER FOR CATHETER TUBES AND THE LIKE

BACKGROUND OF THE INVENTION

1. Field of the Invention

This invention relates to a separable fastener which is in the form of a strap member for encompassing and supporting members such as medical tubes.

2. Description of the Prior Art

Separable fasteners such as those described in U.S. Pat. Nos. 2,717,437 and 3,009,235 which are marketed under the registered trademark VELCRO® brand hook and loop fasteners by Velcro Corporation, 681 Fifth Ave., New York, N.Y. have gained wide acceptance because of the properties of the mating hooks and loops. A surface defined by the hooks is merely placed into face-to-face relationship with a surface defined by the loops so that a large number of hooks engage a large number of loops and therefore are able to resist separation by forces parallel to the interfacial plane of engagement but are readily separable by peeling forces applied substantially normal to this interfacial plane. These fastening devices are generally formed of a sheet of synthetic woven or knitted fabric having raised threads of synthetic material, such as nylon, which are napped or unnapped to provide a pile surface defined by a plurality of loops, and which may be thermally treated to become semi-rigid. Certain of the loops may then be cut along one side near their outer extremity to form hooks.

These fasteners have been utilized in numerous applications in many fields of use, particularly because of their unique touch and close fastener capability as well as their fastening strength. The unique fastening capability of these hook and loop-type engaging elements have been applied to particular uses to create new and unobvious fastener arrangements.

In particular, fasteners of this type have previously been utilized as strapping devices of various types. Although the prior art dealing with straps and the like includes numerous fastener devices of various types to secure the straps in their intended environment, the applications of these separable hook and loop-type fasteners have reduced the need for the traditional strap fastening devices such as buckles and the like. To the extent that the early fastening devices did not generally facilitate variable and precise fastening, the application of these separable fasteners to the strap art has proven to provide substantial advantages.

U.S. Pat. No. 3,000,384 to Piers, Jr., relates to a fastener tie to retain a hank or lock of hair in a desired shape. In an embodiment, a portion of a longitudinally elastic tape is threaded through the opening of an attached elongated eye in such a way that the tape forms a spiral-like configuration. U.S. Pat. No. 3,297,026 to Van Pelt, relates to a restraining device for holding a limb of an anatomical body. The restraining device includes an elongated resilient pad wrapped around a part of a human limb. U.S. Pat. No. 3,726,280 to Lacount relates to a catheter support combining VELCRO® brand fasteners with an elastic band which is secured around the patient's thigh. U.S. Pat. No. 3,827,107 to Moore, relates to an adjustable strap assembly which utilizes VELCRO® brand fasteners in combination with a pad having hooking elements on both sides to eliminate the requirement of an excessively long length of looped strap portion. U.S. Pat. No. 3,878,849 to Muller et al., relates to a surgical tube supporter having an elastic strap with a high friction layer on one face to engage the patient's skin. In still another development, a strap adapted to support surgical tubes is comprised of an elastic strap portion connected at one end to an inelastic strap portion with hook and loop-type fastener tape members attached thereto at the interface between the elastic and inelastic strap portions. An endless ring-like member is utilized to loop the hook fastener tape about the surgical tube to provide support therefor.

Along with the fastening advantages of the prior art, certain disadvantages nevertheless remain, particularly when the fastener device is utilized to support a catheter strap to a patient's limb. For example, in the presently known devices, which utilize elastic bands and the like, there is a tendency to restrict the flow of blood through the encircled human limb and this constriction has been known to cause ulcerations of the limb. Still others neither firmly support and secure the catheter tube to the strap nor the strap to the limb and this failure generally results in pain and discomfort to the patient if the tube slips out of position or becomes otherwise relocated. In addition, the prior art devices do not provide a strap of a fixed length which may be varied in size to accommodate limbs or body portions of numerous sizes. We have invented a relatively inexpensive fastening device in which these disadvantages are successfully avoided and which is particularly useful in providing generally firm but gentle support for catheter tubes and the like.

SUMMARY OF THE INVENTION

The invention relates to a separable fastening device comprising a flexible strap member adapted to support an elongated member such as a catheter tube and the like to another member such as a leg of a patient. The fastening device comprises a flexible strap member including a first flexible strap section having on a first surface portion a plurality of engaging elements upstanding therefrom. The strap member also includes a second flexible strap section having on a surface portion opposite the first surface portion, a plurality of mating engaging elements upstanding therefrom. At least one flexible strap section defines an opening extending therethrough and the opening is dimensioned and spaced sufficiently from the other strap section so as to receive a free end portion of one of the strap sections such that at least a portion of one of the strap sections may be looped about at least a portion of the elongated member and positioned within the opening with the engaging elements of the opposed surfaces positioned in engaged face-to-face relation to support the elongated member.

Although the fastener strap may be of a unitary construction, preferably it is constructed of VELCRO® brand separable fastener tape materials suitably secured to each other to provide the desired arrangement. The separable fastener tape may have a base member, woven or knitted of a synthetic heat deformable material such as nylon, polyester, and the like, having resilient engaging elements upstanding from the respective base member. In the present embodiment, the engaging elements are constructed in the form of hook-type hooking elements which mate with loop-type hooking elements on their opposed engaging surface portions. However, it should be understood that any flexible engaging elements, including mushroom-like elements, resilient projections, etc., which are readily securable in face-to-face relation, and which particularly resist forces parallel to the interfacial plane of engagement, are contemplated within the scope of the present invention, provided the fastener strap is flexible. Such mushroom configured hooking elements as the type disclosed in U.S. Pat. Nos. 3,138,841 and 3,320,649 both to Naimer, and U.S. Pat. Nos. 3,718,725 and 3,770,359 both to Hamano are contemplated. Further examples of knitted form fastener members contemplated within the scope of the present invention are disclosed in U.S. Pat. Nos. 3,530,687 and 3,539,436 both to Hamano.

In the preferred embodiment, the first strap section is comprised of a strip of knitted textile material made from nylon multifilamentary yarns and constructed to have a multiplicity of loop-type filamentary engaging elements upstanding from a surface of the textile material. A polyurethane foam material substrate is secured to the opposite surface of the textile material. The advantages of a strap section having such a foam material substrate are numerous. For example, when a portion of the foam material is looped about an elongated member such as a catheter tube and positioned in contacting, supporting relation therewith, the foam provides a soft, but firm non-slip support for the catheter tube and does not constrict the flow of fluids through the tube. Consequently, when the foam material is placed in encompassing relation about the human limb its frictional resistance and stretchability are such as to firmly secure the tube to the strap and the strap to the limb. The cushioning characteristics of the foam material uniquely prevents the constriction of blood through the encompassed limb while simultaneously providing the necessary support for the tube. Since the porosity of the foam material allows air to circulate therethrough to the limb, it also prevents excoriation of the skin (chafing). The foam material textile combination contemplated in the preferred embodiment is a strap material of approximately ¼ inch thickness and is marked by VELCRO Corporation under the registered trademark VELFOAM.

In a further embodiment of the invention, it has been found to be particularly advantageous to provide a relatively short strip of hook-type fastener tape secured to a surface portion of the foam material near the opening in the first strap member. Thus, when the first strap section is positioned in encircling relation with the member such as a body section or limb, the strip of hook-type fastener tape is conveniently positioned to secure itself to the multifilamentary engaging elements of the first strap section whle the foam material frictionally grips the member to thereby retain the entire fastener in a taut condition thereabout.

The first strap section is advantageously configured with a tapered end portion generally adjacent the end which is connected to the second strap section. In its preferred form, the second strap section is configured and dimensioned such that positioning at least a portion of the tapered end portion of the first strap section about the catheter tube in contacting relation therewith, provides cushioned support for the tube while a portion of the second strap section extends through the opening. The hook-type engaging elements of the portion of the second strap section which extend through the opening, matingly engage the upstanding multifilamentary loop-type engaging elements of the first strap section so as to retain the catheter tube within the cushioned support. It will be seen further that in the preferred embodiment of the invention, the hook fastener tapes, as well as the opening, are configured and disposed generally away from an end portion of the first strap section. Although the hook and loop-type fastener tapes permit adjustability in the size of the strap, the combination of knitted textile fabric and foam material may be readily severed to permit the creation in-situ of several sizes which may accommodate human limbs of various proportions. Thus, a single length fastener may be provided for virtually all limb sizes, taking into consideration, not only the variations from person to person, but also the variations from one type of lime to another, e.g. the variations from legs to arms, etc.

It will be further appreciated that the inventive separable fastening device provides a relatively inexpensive, washable, autoclavable device, and these features are particularly significant when it is constructed to support medical devices such as catheter tubes of all types, particularly Foley Catheters.

It will be further appreciated that in its broadest application, the invention is nevertheless extremely useful for supporting, securing or connecting any object or device to another member or to a frame structure, beam and the like.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

For the purpose of the description which follows, the references to fastener tapes having "hook-type hooking elements" and "loop-type hooking elements" contemplate all such separable fastener tapes of the "press to close, peel to open" type. For example, engaging elements of the loop-type may include filamentary hooking elements upstanding from a surface of the fastener tape, as well as engaging elements in the form of loops per se upstanding from such tapes. Further, hooking elements of the hook-type, contemplate such engaging elements as mushroom, burrs and the like, as well as hooks per se upstanding from a surface of the fastener tape.

Figure 1:
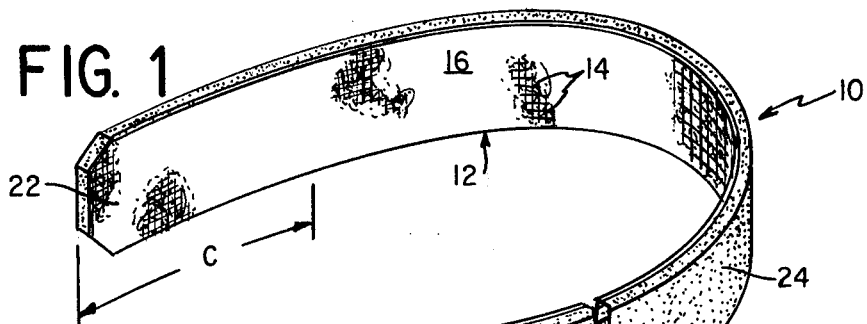
FIG. 1 is a perspective view of the separable fastening strap of the present invention.

Referring to FIG. 1, there is illustrated a separable fastening device 10 in the form of a strap member comprised of a first strap section 12 having a knitted fastener tape 16 and a plurality of resilient loop-type hooking elements 14 upstanding from one surface of the fastener tape 16. A second strap section 20 has a plurality of mating hook-type hooking elements 18 upstanding from a surface thereof which is positioned opposite to the loop-type hooking surface of tape 16 of the first section 12. The first and second strap sections may be entirely integrally constructed or connected by sewing, welding, gluing, etc. In the preferred form, they are attached to each other as shown by pressing the mating surfaces of two respective end portions together. The knitted loop fastener tape 16 is preferably of the type marketed under the trade name "V22-70" and is attached at 21 to a separate length of VELCRO ® brand hook fastener tape 18 such that the loop elements 14 of the knitted tape 16 and the hook elements 18 of the other tape 20 face in opposite directions.

Referring further to the drawings, the VELCRO ® brand hook fastener 20 has a woven nylon base and resilient hooking elements 18 upstanding therefrom. The loop fastener tape 16 of the other section consists of a Tricot knit nylon textile material having a plurality of multifilamentary nylon yarns 14 upstanding from one surface. The multifilamentary yarns are interknitted into the base member with floating stitches and the material is thereafter brushed or napped to cause the multifilamentary yarns to stand and appear as a fuzzy, pile surface which has been found to conveniently engage the VELCRO ® brand hook fastener tape in a manner similar to the engagement with VELCRO ® brand woven loop material. While this filamentary brushed surface does not provide the same holding power as VELCRO ® brand fastener tape (i.e. having actual loops upstanding from one surface), its relatively inexpensive knitted character has been found to provide holding capability which is sufficient for use in supporting numerous types of medical devices as will be seen in the description as it develops.

Referring once again to FIG. 1, strap section 12 is constructed of a layer of polyurethane foam 24 secured by flame lamination to the base of the VELCRO ® brand V22-70 loop fastening tape 16. the combination of multifilamentary yarn material V22-70 with the polyurethane foam material is a stretchable foam backed material known as VELFOAM ® having somewhat elastic properties and is commercially available through the VELCRO ® brand fastener tape distribution system.

Figure 2:
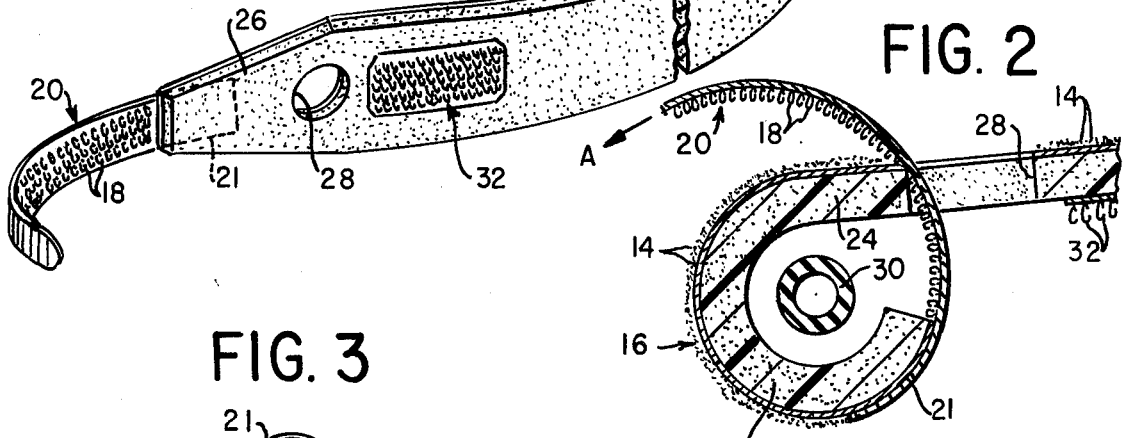
FIG. 2 is a cross-sectional view of the separable fastening strap of FIG. 1 illustrating the preferred technique for encompassing and securing the catheter tube.
Figure 3:
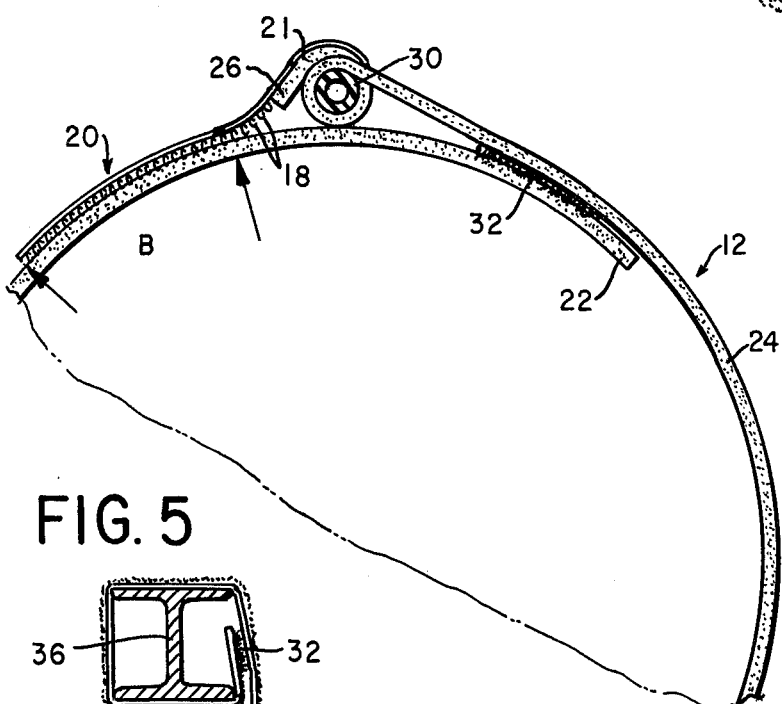
FIG. 3 is a side view of the separable fastening strap of FIG. 1 supporting a catheter tube encompassed and secured according to the present invention.

The strap section 12 has a tapered end portion 26 and defines an opening 28 extending through the knitted fastener and foam materials and spaced generally adjacent the tapered portion such that the free end of the other strap section 20 may encircle catheter tube 30 and pass through the opening 28 as shown particularly in FIGS. 2 and 3. The opening 28 is configured and sufficiently dimensioned to accept the free end of the strap section 20 as shown. Furthermore, the tapered configuration of the end portion of strap section 12 facilitates insertion thereof through the opening 28 with strap section 20. As will become readily apparant to persons skilled in the art, the opening may be alternately located in the second strap section 20 with the free end of the second strap section passing therethrough.

As further shown in FIG. 1, strap section 12 has secured to its foam side a separate length of VELCRO ® brand hook fastener tape 32. A third section 32 of fastener tape having hook-type hooking elements upstanding from one surface is positioned generally adjacent the opening 28 as shown and is glued to the foam material. Alternately, other suitable known securing techniques may be utilized such as flame lamination, etc.

As shown in FIGS. 2 and 3, catheter tube 30 is positioned adjacent the surface of the foam material 24 of strap section 12 between the tapered end and the opening 28. A portion of the hook fastening tape of strap section 20 and the foam material 24 of strap section 12 encircles the catheter tube 30 in a firm, but gentle manner. The major portion of the free end of strap section 20 extends through the opening 28 as shown and is conveniently positioned to be mated with the loop elements of the engaging surface of strap section 12 to thereby define an endless loop comprised of the tapered end portion of the strap section 12 looped upon itself. As strap section 20 is pulled in the direction of arrow "A" in FIG. 2, the endless loop formed thereby tightens and firmly secures itself around the tube 30 while the endless loop is formed with the foam surface 24 of the strap section 12 in contiguous relation with the tube 30.

Referring now to FIG. 3, the endless loop of strap section 12 is shown tightly wrapped about the catheter tube 30. Although the entire strap section 20 is shown extending through the opening 28, this is not necessary. It is sufficient to extend a free end portion of strap 20 through opening 28 to facilitate mating engagement of the surfaces of the strap sections. In FIG. 3, a part of the tapered portion 26 of the first strap section also extends through the opening 28 although this is also not necessary. However, as in the case of the strap 20 the passage through the opening of a substantial portion of the tapered portion of strap section 12 is desirable since it enhances the securing of the endless loop about the catheter tube 30.

In FIG. 3, the free end portion of the second strap section 20 is shown releasably attached to a portion of the strap section 12 at location "B". The hook-type elements of the strap section 20 are pressed into face-to-face relation with the mating engaging loop-type elements of the strap section 12. By releasably attaching together the mating engaging elements of these two strap sections, a second generally endless loop is created which secures and encompasses the leg as shown in FIG. 4.

The foam material acts as a soft, but firm support having a friction surface which comfortably encompasses the limb and thereby prevents the tube from slipping out of its respective endless loop. Since the foam surface is porous and breathable, the chances of producing ulcerations on an encircled human limb are minimized. The foam material also prevents the skin from chafing since it is breathable and resilient and it allows air to circulate to the skin, yet has sufficient frictional resistance and stretchability so as to firmly secure itself about the human limb. Furthermore, the cushioning property of the foam material prevents the constriction of the blood circulating through an encompassed limb, as well as preventing the crushing of an encircled catheter tube. In addition, the combination of the variable and precise fastening capabilities of the VELCRO ® brand fastener tapes with the cushioning characteristics of the foam material prevents constriction of blood flow through an encompassed leg or arm.

Referring once again to FIGS. 1 and 3, it can be seen that the free end portion "C" of strap section 12 may be easily cut with a pair of scissors to reduce the size of the fastener. Advantageously, the various VELCRO ® brand hook fastener tapes, as well as opening 28 are disposed generally away from the free end portion 22 of the strap section 12 and these features facilitate the cutting of strap section 12 to accommodate the broad range of human limb sizes from patient to patient and from arm sizes to leg sizes.

Figure 4:
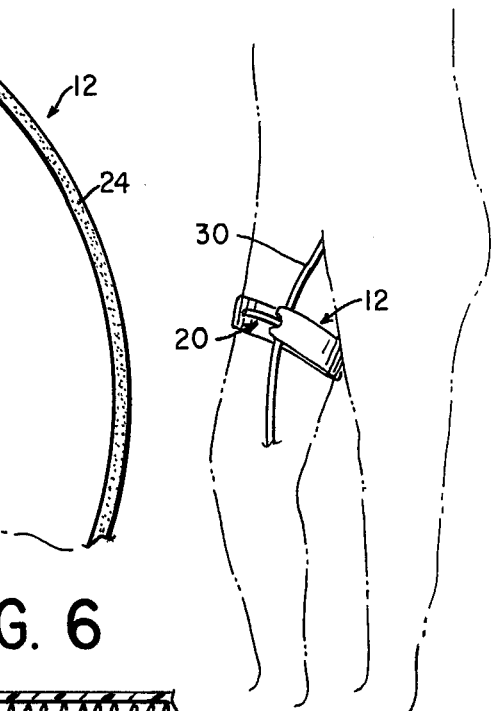
FIG. 4 is a side view of the lower portion of the human body illustrating the use of the separable fastening device as a catheter strap.

Referring to FIG. 4, the fastening device of FIGS. 1 through 3 is secured to the right thigh of a patient and adapted to support a catheter tube 30. The catheter tube 30 is shown secured and supported by the endless loop previously described. A second endless loop encircles the thigh as shown, and the strap section 20 is releasably attached to the strap section 12. The unique configuration of the present invention thereby prevents the catheter tube from riding up, down, or sliding across the patient's thigh. Thus, the painful movement of an unsecured catheter tube is easily and economically eliminated by the present invention. In addition, it has been found that the gentle and firm support provided for the catheter tube is such that it is capable of maintaining the tube in traction where this may be required.

Figure 5:
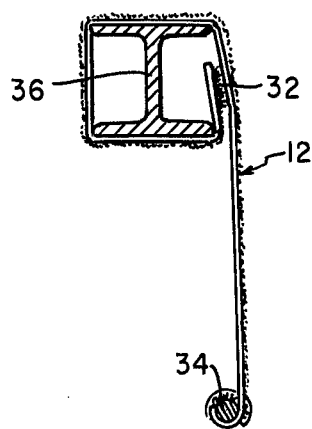
FIG. 5 is an illustration of an alternate application of the separable fastening strap to secure a rod to a structure.
Figure 6:
FIG. 6 is a cross-sectional view of a hook and loop-type separable fastener device having hook-type hooking elements on one surface and loop-type hooking elements on the other.

Although the present fastener device is preferably adapted to support catheter tubes of various types, it should be understood that the unique arrangement is adaptable for supporting any object to a structural member without departing from the scope of the invention. For example, in FIG. 5, the tapered end portion of strap section 12 is encircled about a rod or bar 34 to support the rod in a manner similar to the support of the catheter tube 30. The other end portion of strap section 12 is looped about the structural beam 36 to form an endless loop thereabout, and the loop fastener surface of strap section 12 is secured to the hook fastener tape 32.

Accordingly, it is significant to note that numerous other fastener applications will immediately be foreseen by those skilled in the art. For example, the present fastener is suitable for use in EKG straps, I.V. tube straps, wrist and ankle restraints, arm slings, anesthetic gas delivery hose straps, conduit or cable supports, flower pot hangers, utensil or pencil holders for handicapped persons, structural devices, etc. While other types of straps may be used for the above application, it has been found that the unique configuration of the present invention makes it possible to firmly secure and support delicate members relatively inexpensively and avoid any real or potential problems of crushing these members. Furthermore, as can be seen from the foregoing, the supporting and securing is accomplished in an improved manner notwithstanding the fact that the members to be secured have irregular, nonconforming configurations.

It will also be understood that the separable fastening device may be constructed of VELCRO ® brand hook and loop-type fastener straps in which the straps exhibit flexible, elastic properties in at least one direction. Such fastener tapes may be fabricated from elastic material such as natural or synthetic rubber or rubber based yarn, generally in the warp direction so as to provide elasticity at least along the length of the fastener tape.

We claim:

1. A separable fastening device adapted to support an elongated member such as a catheter tube and the like which comprises a flexible strap member including first flexible strap section having first and second end portions and having on one surface portion a plurality of engaging elements upstanding therefrom, a second elongated flexible strap section having on a surface portion opposed to said first surface portion a plurality of mating engaging elements upstanding therefrom, said second strap section being detachably joined at one end portion to the first end portion of said first strap section and extending generally longitudinally therefrom by engagement of the engaging elements of said strap sections, the other end of said second strap section being free, said first flexible strap section defining an opening extending therethrough at a location generally adjacent said first end portion, said opening being dimensioned and spaced sufficiently from said second strap section to receive said free end portion of said second strap section such that at least a portion of said second strap section may be looped at least a portion of said elongated member and positioned within said opening with the engaging elements of said opposed surfaces positioned in engaged face-to-face relation to support said elongated member.

2. A separable fastening device adapted to support a medical device such as a catheter tube and the like which comprises a flexible strap member including a first strap section having first and second end portions and having on a first surface portion a plurality of resilient engaging elements of the hook and loop-type upstanding therefrom, a second flexible strap section having on a surface portion opposed to said first surface portion a plurality of resilient mating engaging elements upstanding therefrom, said second strap section being detachably joined at one end portion of said first strap section and extending generally longitudinally therefrom by engagement of the engaging elements of said strap sections, the other end of said second strap section being free, said first flexible strap section defining an opening extending therethrough at a location generally adjacent said first end portion, said opening being dimensioned and spaced sufficiently from said second strap section to receive said free end portion of said second strap section such that at least a portion of said second strap section may be looped about at least a portion of said medical device in supporting contacting relation therewith and positioned within said opening with at least portions of the mating engaging elements of said opposed surfaces positined in engaged face-to-face relation to retain and support said medical device.

3. The separable fastening device according to claim 2 wherein at least one of said strap sections comprises at least one of a woven and knitted base material.

4. The separable fastening device according to claim 3 wherein said base material comprises at least one of a woven and knitted nylon material.

5. The separable fastening device according to claim 4 wherein at least one strap section is comprised of a textile material having a plurality of resilient engaging elements upstanding from one surface and a foam material substrate secured to an opposite surface.

6. The separable fastening device according to claim 5 wherein said foam material substrate is polyurethane foam.

7. The separable fastening device according to claim 6 wherein said textile material comprises a strip of multifilament yarn textile material.

8. The separable fastening device according to claim 7 wherein the engaging elements are in the form of resilient loop-type hooking elements upstanding from the first surface portion of the first strap section and the mating engaging elements are in the form of resilient hook-type hooking elements upstanding from the surface of the second strap section opposite said first surface portion of said first strap section.

9. The separable fastening device according to claim 8 wherein said strap sections are joined by engagement of the loop-type hooking elements with the mating hook-type hooking elements such that the loop-type hooking elements of the first strap section and the hook-type hooking elements of the second strap section face in opposite directions.

10. The separable fastening device according to claim 9 wherein said resilient loop-type hooking elements comprise a knitted multifilament yarn material.

11. The separable fastening device according to claim 10 wherein said first strap section comprises a plurality of mating engaging elements upstanding from a surface portion of said foam material opposite the strip of the multifilament textile material.

12. The separable fastening device according to claim 11 wherein the mating engaging elements upstanding from the surface portion of said foam material comprises hook-type hooking elements such that encircling said fastening device about an elongated member such as a human limb permits engagement of said hook-type hooking elements with said multifilament loop-type hooking elements to secure said device in position about said member.

13. The separable fastening device according to claim 12 wherein a strip of hook-type fastener tape is secured to the surface portion of said foam material at a location spaced from the joinder portion of said strap sections and opposite said first surface portion of loop-type hooking elements.

14. The separable fastening device according to claim 13 wherein said first strap section having multifilament loop-type hooking elements defines the opening and said opening is spaced from the joinder portion of said strap sections.

15. The separable fastening device according to claim 14 wherein said second flexible strap section is dimensioned and sufficiently elongated for said free end portion thereof to extend through said opening defined by said first strap section to facilitate mating engagement of said hook-type hooking elements of said second strap section with said loop-type hooking elements of said first strap section.

16. The separable fastening device according to claim 15 wherein said first end portion of said first strap section has a generally tapered configuration and said opening defined by said first strap section is dimensioned to receive at least a portion of said tapered end portion such that the looping of said second strap section and a portion of said tapered end portion through said opening defines a generally endless support means to encompass said medical device.

17. The separable fastening device according to claim 16 wherein said first strap section defines said opening generally adjacent the joinder portion of said first strap section and said second strap section.

18. A fastener for supporting an object which comprises an elongated flexible strap member having on opposite surfaces thereof interengagable mating surfaces including a first strap section and a second strap section, said first strap section having first and second end portions and being provided with a multiplicity of loop-type hooking elements upstanding therefrom, said first strap section having a foam material substrate secured to a surface portion opposite the surface portion of hook-type hooking elements; said second strap section having first and second end portions and being provided with a multiplicity of hook-type hooking elements upstanding therefrom, said first end portion of said second strap section being detachably joined to the first end portion of said first strap section by the engagement of said hooking elements of said strap sections, the second end portion being free, said first end portion of said first strap section defining an opening therethrough, said opening being dimensioned sufficient to receive said second free end portion of said second strap section when said second strap section is positioned in surrounding relation about the object to be supported, said surrounding relation being retained by engagement of said mating engaging surfaces.

19. A separable fastening device adapted to support a catheter tube in adjacent relation to a portion of a human body such as a limb which comprises:
   a. a first flexible elongated strap section having:
      1. a layer of foam material substrate; and
      2. a textile material of knitted multifilamentary yarns having a multiplicity of loop-type filamentary engaging elements upstanding from the surface thereof, an opposite surface of said textile material being secured to one surface of said foam substrate, said foam substrate and textile material having at least one tapered end portion and defining an opening generally adjacent said tapered end portion thereof;
   b. a second flexible strap section having a plurality of hook-type engaging elements upstanding from one surface and secured to the tapered end portion of said first strap section, said second strap section being configured and dimensioned such that encircling at least a portion of said tapered end portion of said first strap section about the catheter tube with the foam material substrate in contacting relation therewith provides firm, but gentle cushioned support for the catheter tube while extending said second strap section through the opening facilitates mating engagement of the hook-type engaging elements of said second strap section with said upstanding multifilamentary loop-type engaging elements of said first strap section; and
   c. a third section of fastener tape having a multiplicity of upstanding hooking elements of the hook-type secured to a surface of the foam material adjacent the tapered end portion such that the strap sections may be encircled about the limb in a manner to position the hook and loop-type engaging elements in engaged relation to retain said strap sections in a predetermined tensioned condition about the limb, while said hook and loop-type engaging elements of said first and second strap sections facilitate maintenance of said tension and completion of said attachment about the limb.

20. A catheter tube support which comprises a flexible strap member including:
   a. a first strap section having a first end portion, at least a portion of which is generally tapered and a second end portion, said first strap section comprising a strip of multifilament yarn textile material having a plurality of loop-type resilient engaging hooking elements of knitted multifilament yarn material upstanding from one surface and a polyurethane foam material substrate secured to an opposite surface, said first strap section defining an opening therethrough spaced from said first end portion;
   b. a second elongated, flexible strap section of a woven or knitted nylon base material having a plurality of mating hook-type resilient engaging hooking elements upstanding from a surface opposite said surface of loop-type hooking elements of said first strap section, said second strap section being joined at one end to said first end portion of said first strap section by engagement of said loop-type and hook-type hooking elements the other end of said second strap section being free, said second strap section and said opening in said first strap section being dimensioned for reception of said free end portion of said second strap section and at least a portion of said first tapered end portion of said first strap section such that the looping of said second strap section and a portion of said first tapered end portion through said opening defines a generally endless support means to encompass said catheter tube; and c. a strip of hook-type fastener tape secured to a surface portion of said foam material substrate at a location spaced from the first tapered end portion and opposite said surface of loop-type hooking elements of said first strap section such that encircling an end portion of said first strap section about a human limb permits engagement of said hook-type hooking elements of said hook-type fastener tape with said loop-type hooking elements to secure said catheter tube in position about said limb.

21. The separable fastening device according to claim 20 wherein said first strap section defines said opening generally adjacent the joinder portion of said first strap section and said second strap section.

* * * * *

UNITED STATES PATENT AND TRADEMARK OFFICE
CERTIFICATE OF CORRECTION

PATENT NO. : 4,088,136
DATED : May 9, 1978
INVENTOR(S) : Russell Hasslinger et al.

It is certified that error appears in the above-identified patent and that said Letters Patent are hereby corrected as shown below:

Column 3, line 38, "marked" should read -- marketed --

Column 3, line 50, "whle" should read -- while --

Column 5, line 16, "hook fastener 20" should read -- hook fastener tape 20 --

Column 8, line 9 (Claim 1, line 21) "at least a portion" should read -- about at least a portion --.

Column 9, line 35 (Claim 15, line 4) "end portion thereot" should read -- end portion thereof --

Signed and Sealed this

Thirty-first Day of October 1978

[SEAL]

Attest:

RUTH C. MASON
Attesting Officer

DONALD W. BANNER
Commissioner of Patents and Trademarks